US011471290B2

United States Patent
Nelson et al.

(10) Patent No.: US 11,471,290 B2
(45) Date of Patent: Oct. 18, 2022

(54) COUNTER-TORQUE REVISABLE STEMLESS SHOULDER IMPLANT

(71) Applicant: Howmedica Osteonics Corp., Mahwah, NJ (US)

(72) Inventors: Andrew J. Nelson, New City, NY (US); Daniel E. Sapio, Mohegan Lake, NY (US); Manoj Kumar Singh, Mahwah, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 14 days.

(21) Appl. No.: 16/923,604

(22) Filed: Jul. 8, 2020

(65) Prior Publication Data

US 2021/0007856 A1 Jan. 14, 2021

Related U.S. Application Data

(60) Provisional application No. 62/872,319, filed on Jul. 10, 2019.

(51) Int. Cl.
| | |
|---|---|
| *A61F 2/40* | (2006.01) |
| *A61F 2/46* | (2006.01) |
| *A61F 2/30* | (2006.01) |

(52) U.S. Cl.
CPC .......... *A61F 2/4003* (2013.01); *A61F 2/4612* (2013.01); *A61F 2/4637* (2013.01); *A61F 2002/30525* (2013.01); *A61F 2002/30884* (2013.01)

(58) Field of Classification Search
CPC .... A61F 2/4003; A61F 2/4612; A61F 2/4637; A61F 2002/30884; A61F 2002/30525; A61F 2002/30561; A61F 2/30749
See application file for complete search history.

(56) References Cited

U.S. PATENT DOCUMENTS

| | | |
|---|---|---|
| 2012/0041564 A1 | 2/2012 | Landon |
| 2018/0271668 A1 | 9/2018 | Kemp et al. |
| 2018/0333268 A1* | 11/2018 | Cardon ................. A61F 2/4081 |

* cited by examiner

*Primary Examiner* — Yashita Sharma
*Assistant Examiner* — Jared Klar Rovira
(74) *Attorney, Agent, or Firm* — Lerner, David, Littenberg, Krumholz & Mentlik, LLP (57) ABSTRACT

A base member of a prosthetic stemless shoulder implant may include a proximal collar, a central anchor, and at least one peripheral anchor. The proximal collar may have a proximal surface and a distal bone-engaging surface opposite the proximal surface. The central anchor may extend distally from the bone-engaging surface and define an opening extending from the bone-engaging surface into the central anchor for receiving a humeral head component of the prosthetic stemless shoulder implant. The at least one peripheral anchor may be positioned radially outwardly of the central anchor and extend distally from the bone-engaging surface. The peripheral anchor may be frangibly connected to the proximal collar.

20 Claims, 7 Drawing Sheets

COUNTER-TORQUE REVISABLE STEMLESS SHOULDER IMPLANT

CROSS REFERENCE TO RELATED APPLICATIONS

This application claims the benefit of the filing date of U.S. Provisional Patent Application No. 62/872,319, filed Jul. 10, 2019, the disclosure of which is hereby incorporated by reference as if fully set forth herein.

BACKGROUND OF THE DISCLOSURE

Over time and through repeated use, bones and joints can become damaged or worn. For example, repetitive strain on bones and joints (e.g., through athletic activity), traumatic events, and certain diseases (e.g., arthritis) can cause cartilage in joint areas, for example, which normally provides a cushioning effect, to wear down. When the cartilage wears down, fluid can accumulate in the joint areas resulting in pain, stiffness, and decreased mobility. The same can happen in cases where tendons in a joint become lax or soft tissues in or adjacent the joint become damaged or worn.

Arthroplasty procedures can be used to repair such damaged joints. During a typical arthroplasty procedure, an arthritic or otherwise dysfunctional joint can be remodeled or realigned. A prosthesis or prostheses can be implanted to repair the damaged region(s). Arthroplasty procedures may take place in any of a number of different regions of the body, such as the knees, hips, shoulders, or elbows, for example. One type of arthroplasty procedure is a shoulder arthroplasty, in which a damaged shoulder joint may be replaced with prosthetic implants. The shoulder joint may have been damaged by, for example, arthritis (e.g., severe osteoarthritis or degenerative arthritis), trauma, or a rare destructive joint disease.

Prostheses that are implanted into a damaged region may provide support and structure to the damaged region, and may help to restore the damaged region, thereby enhancing its functionality. Prior to implantation of a prosthesis in a damaged region, the damaged region may be prepared to receive the prosthesis. In the case of a shoulder arthroplasty procedure, one or more of the bones in the shoulder area, such as the humerus and/or glenoid, may be treated (e.g., cut, drilled, reamed, and/or resurfaced) to provide one or more surfaces that can align with the implant and thereby accommodate the implant.

It is often preferable to maintain as much of a patient's natural bone stock as possible during such a procedure. Prostheses generally have a certain life expectancy and in certain cases need to be replaced at some point. If one or more primary prostheses need to be removed and/or replaced in a revision procedure, a large bone void could be left after the removal of the primary implant. In certain cases, this large bone void is not ideal for receipt of revision components. For example, if removal of the primary prosthesis results in significant loss of bone stock, the remaining bone stock may not be able to provide enough support for the secondary prosthesis to be implanted during the revision procedure. Thus, preserving natural bone stock may be desirable for the ability to suitably perform a revision procedure.

In total or partial arthroplasty surgery, stemmed prostheses are often used which generally include a long stem that passes through a center of a long bone, the stem helping to anchor the components of the prosthesis. However, stemmed prostheses may result in a large amount of healthy bone being removed in order to accommodate the stem. In some cases, stemless prostheses may be used, which may result in less healthy bone stock being removed. However, in some cases stemless prostheses may not anchor the particular prosthesis as well as a stemmed prosthesis would. In addition, some stemless shoulder prostheses may require the removal of significant proximal humeral bone if a revision procedure is to be performed, which may compromise the proximal humerus and result in more challenging revision surgeries.

BRIEF SUMMARY OF THE DISCLOSURE

In accordance with an aspect of the present disclosure, a base member for a joint implant may include an anchor portion and a collar for retaining a stem of an implant. The anchor portion and the collar may be joined by frangible portion. The frangible portion may be significantly more resilient with respect to linear loads, such as shear or axial loads, than with respect to torque. The base member may therefore be durable within a joint in use while permitting the collar to be easily separable from the anchor portion when a revision of the joint becomes necessary. Alternatively, the frangible portion may include features that cause the frangible portion to fracture upon application of a certain tool or force. Removal of the collar from the anchor portion may provide clear access to the anchor portion to improve preservation of bone during removal of the base member. The anchor portion and collar may both have engageable features to permit application of torque or other differential force between the anchor portion and collar, and tools may be provided for application of force through the engageable features.

In another aspect, a base member of a prosthetic stemless shoulder implant may include a proximal collar, a central anchor, and at least one peripheral anchor. The proximal collar may have a proximal surface and a distal bone-engaging surface opposite the proximal surface. The central anchor may extend distally from the bone-engaging surface and define an opening extending from the bone-engaging surface into the central anchor for receiving a humeral head component of the prosthetic stemless shoulder implant. The at least one peripheral anchor may be positioned radially outwardly of the central anchor and extend distally from the bone-engaging surface. The peripheral anchor may be frangibly connected to the proximal collar.

In some arrangements, the at least one peripheral anchor may be frangibly connected to the central anchor.

In some arrangements, the proximal collar and the central anchor may be separable from the at least one peripheral anchor upon application of a threshold torque force.

In some arrangements, the threshold force may be at least ten times an axial strength of a frangible portion connecting the proximal collar and central anchor to the at least one peripheral anchor.

In some arrangements, a frangible portion may connect the bone-engaging surface and the at least one peripheral anchor.

In some arrangements, the frangible portion may be configured to break upon application of a threshold torque force.

In some arrangements, the frangible portion may be a material with greater porosity than the proximal collar and the peripheral anchor.

In some arrangements, a hole may extend from the proximal collar into the at least one peripheral anchor for receiving a holding device to prevent rotation of the at least one peripheral anchor.

In some arrangements, the base member may be monolithically formed.

In some arrangements, the base member may include a residual portion that may include the at least one peripheral anchor and a ring that encircles at least one of the proximal collar and the central anchor.

In some arrangements, the ring may be connected to at least one of the proximal collar and the central anchor by a frangible portion.

In some arrangements, the frangible portion may be in the shape of a ring around the at least one of the proximal collar and the central anchor.

In some arrangements, the proximal collar, the central anchor, and the at least one peripheral anchor may include a same material.

In some arrangements, the proximal collar may include a drive channel that may be concentric with the proximal collar for receiving a polygonal drive element.

In some arrangements, the base member may be additively manufactured.

In another aspect, a method of preparing a patient for revision surgery of a prosthetic shoulder implant previously implanted into a patient may include applying torque to a proximal collar of a base member of the prosthetic shoulder implant to break a frangible portion of the base member, thereby separating a proximal collar from at least one peripheral anchor of the base member. The proximal collar may be removed from a humerus of the patient. After the collar is removed, the at least one peripheral anchor may be removed from the humerus of the patient.

In another aspect, the method may include application of a chisel piece to the frangible portion to weaken the frangible portion.

In another aspect, applying the torque may include applying at least one tool to the base member such that a first feature of the at least one tool engages the proximal collar and a second feature of the at least one tool engages a residual portion that includes the at least one peripheral anchor.

In another aspect, the at least one tool may include a lever that engages the proximal collar and a fulcrum that engages the residual portion.

In another aspect, the tool may include a gearbox, a central gear, and an input gear. The gearbox may engage the residual portion. The central gear may be disposed within the gearbox at a location concentric with the proximal collar. The input gear may be operatively connected with the central gear such that rotating the input gear causes the central gear to rotate relative to the gearbox.

DETAILED DESCRIPTION

It should be understood that although the term "stemless implant" is used herein, the term does not indicate that a stemless implant fully lacks any anchor, but rather a stemless implant may include an anchor that is significantly smaller and/or shorter than stems of typical known stemmed implants. Further, the stemless implants of the present disclosure generally include a base member intended for coupling to an end of a first bone of a joint, such as a humerus or femur, and an articulating member intended to attach to the base member and to provide articulation with the second bone of the joint (or a corresponding prosthesis attached to the second bone). Further, as used herein, the term "proximal" refers to a location closer to an individual's heart, and the term "distal" refers to a location farther away from the individual's heart. When used in the context of an implant, the terms "proximal" and "distal" refer to locations on the implant closer to, or farther away from, the heart when the implant is implanted in an intended manner.

Figure 1:
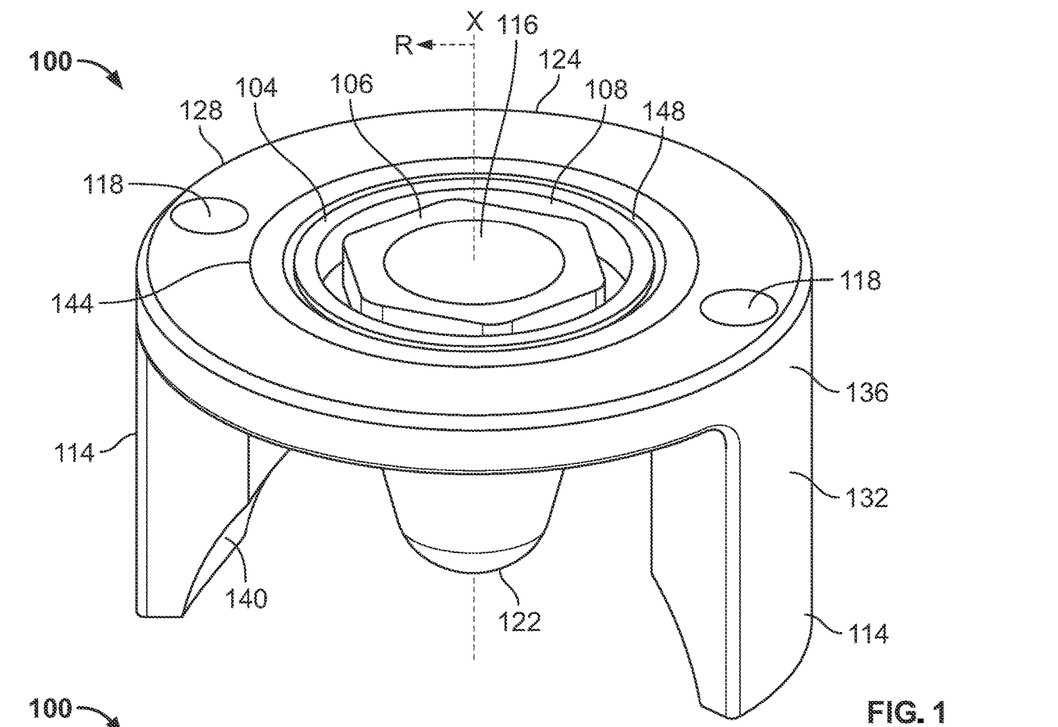
FIG. 1 is an oblique view of an implant base member according to an embodiment.
Figure 2:
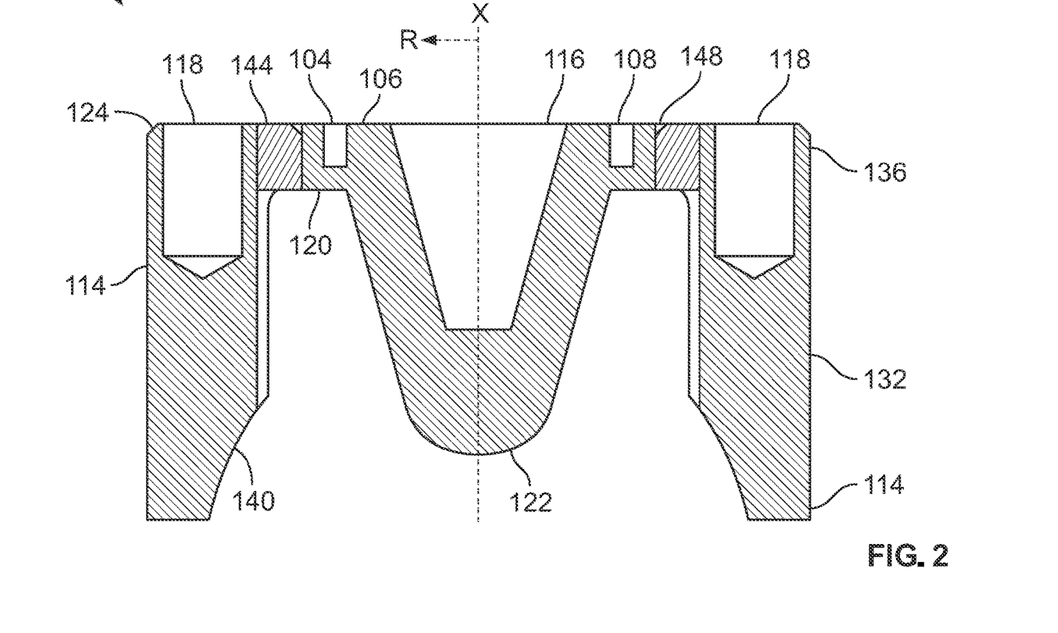
FIG. 2 is a sectional view of the base member.

FIGS. 1 and 2 show a base member 100 of a stemless implant according to a first aspect of the disclosure. Referring specifically to FIG. 1, the base member 100 includes a proximal collar 104 having a proximal surface 106. The proximal surface 106 generally extends across a plane perpendicular to a central longitudinal axis X of the base member 100. A radial direction R is defined on the plane orthogonal to the longitudinal axis X. A hex shaped drive channel 108 is recessed axially into the proximal surface 106 and centered on the longitudinal axis X. As is described in greater detail below, the hex shape of the drive channel 108 is adapted to allow torque to be transmitted from a tool to the drive channel 108. Thus, the hex shape of the illustrated embodiment is merely exemplary, and drive channels 108 of other shapes that allow transmission of torque are contemplated. The collar 104 also includes an opening 116 for receiving an implant component such as, for example, a humeral head component of a shoulder prosthesis. For example, a prosthetic humeral head component may include a spherical, hemispherical, or similarly shaped articulating surface adapted to engage with and articulate with respect to a native glenoid or a prosthetic glenoid of the patient. The prosthetic humeral head component may include an opposing pin or bolt having a male Morse taper adapted to be received within the opening 116, which may include a female Morse taper to allow for locking of the prosthetic humeral head to the base 100 after the base 100 is implanted into a patient. According to the illustrated embodiment, the opening 116 is generally cone-shaped, although the shape may include a female Morse taper as noted above, and centered on the longitudinal axis X of the base member 100. Also according to the illustrated embodiment, the opening 116 extends distally along the longitudinal axis X from the proximal surface 106 through the collar 104. However, other embodiments with differing shapes and locations for an opening 116 suitable for receiving an implant component are contemplated.

The collar 104 further includes a distal or bone engaging surface 120, best illustrated in FIG. 2. A central anchor 122 may extend distally from the bone engaging surface 120. According to the illustrated embodiment, the central anchor 122 generally corresponds to the opening 116 and similarly is of a cone shape and extends along the longitudinal axis X. Other embodiments with differing shapes and locations for a central anchor 122 suitable for engaging cancellous bone are contemplated. Central anchor 122, along with peripheral anchors 114 described below, may provide for an initial fixation of the base 100 to the proximal humerus. Over time, bone ingrowth with the base 100 may further secure the base 100 to the proximal humerus. Central anchor 122 may include various additional or alternative features to provide for additional stabilization and to promote bone ingrowth. For example, the central anchor 122 and distal surface 120 may have different textures, including porous metal coatings such as porous titanium, as well as other shapes such as fins or flutes. Various types of anchor mechanisms, including central anchors and peripheral anchors, that may be suitable for use with base 100 are described in U.S. Patent Publication No. 2018/0271668, the disclosure of which is hereby incorporated by reference herein.

The base member 100 further includes a residual peripheral portion 124 distinct from the collar 104. The residual peripheral portion includes peripheral anchors 114 and counter-torque holes 118. In the illustrated embodiment, the counter-torque holes 118 are aligned with and extend axially into the peripheral anchors 114 from a proximal surface of the residual peripheral portion 124. However, counter-torque holes 118 in other embodiments are located elsewhere on the residual peripheral portion 124. The residual peripheral portion 124 further includes a peripheral ring 128 that connects the peripheral anchors 114 and encircles the collar 104. According to the illustrated embodiment, each peripheral anchor 114 has an axially extending exterior surface 132 that is radially aligned with an outer circumference 136 of the peripheral ring 128. Each peripheral anchor 114 may also include an axially extending interior surface that is substantially parallel to the exterior surface 132. Also according to the illustrated embodiment, each peripheral anchor 114 has an arc shaped transition surface 140 connecting the exterior surface 132 to the interior surface, as best shown in FIG. 2. Again, other embodiments with differing shapes, numbers, and locations of peripheral anchors suitable for engaging bone are contemplated.

The collar 104 is joined to the residual peripheral portion 124 by a frangible portion 144 such that the base member 100 is of a monolithic structure. According to the illustrated embodiment, the frangible portion 144 is in the shape of a ring around the collar 104 and central anchor 122. Also according to the illustrated embodiment, the frangible portion 144 includes a triangular or wedge shaped recess 148 near to or adjoining the outer periphery of the collar 104. The recess 148 provides a relative weak point in the frangible portion 144 to facilitate intentional breakage of the frangible portion 144. The recess 148 may also provide a locating surface for a tool to engage, the tool intended to break the frangible portion 144, described in greater detail below.

Figure 3A:
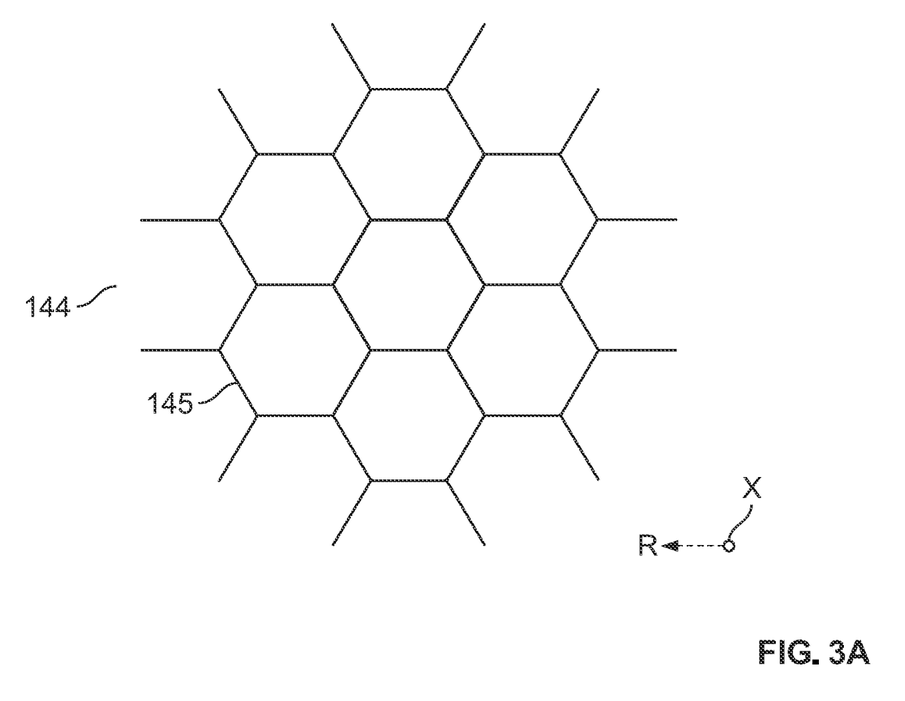
FIG. 3A schematically illustrates part of a frangible portion according to an embodiment.
Figure 3B:
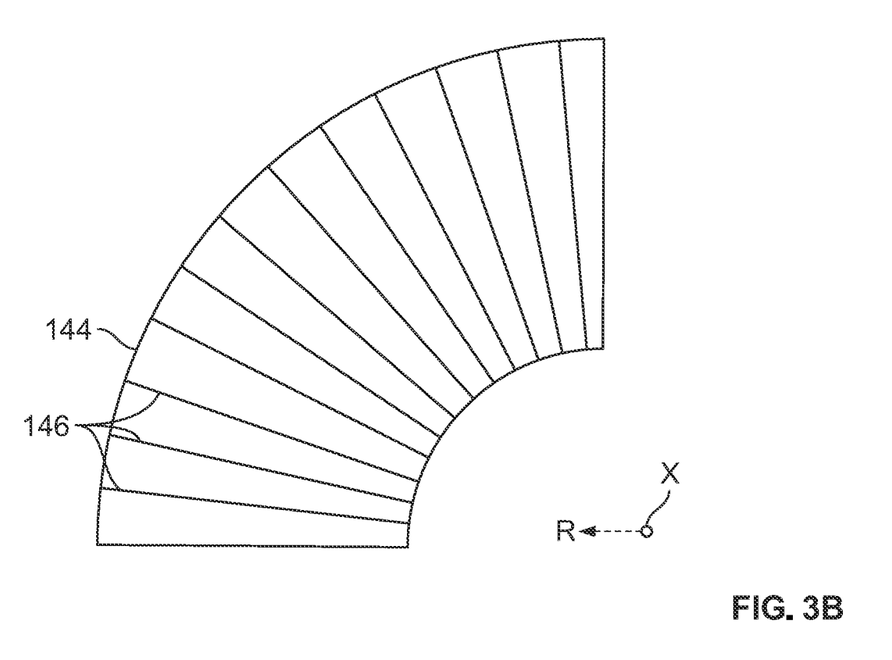
FIG. 3B schematically illustrates part of the frangible portion according to another embodiment.

FIGS. 3A and 3B schematically illustrate a close view of a section of the frangible portion 144 according to differing exemplary embodiments. In the embodiment illustrated in FIG. 3A, the frangible portion 144 has a honeycomb pattern 145 defining channels extending parallel to the longitudinal axis X. In the embodiment of FIG. 3B, the frangible portion 144 includes several blades 146 extending radially and axially. The blades 146 radiate outward from the longitudinal axis X. Either of the patterns shown in FIGS. 3A and 3B will have significantly greater axial and shear strength than torque strength if constructed from any of several known materials typically used in surgical implants, including metals such as titanium.

The frangible portion 144 may be composed of a porous structure or lattice, which may be additively manufactured. For example, the frangible portion 144 may be additively (or otherwise) manufactured to have an increased porosity and/or decreased density compared to the collar 104 and the residual peripheral portion 124. In other words, the entire implant may be formed via additive manufacturing, with the collar 104 and residual peripheral portion 124 having similar qualities to one another, with the frangible portion 144 formed to be weaker than the collar 104 and the residual peripheral portion 124. The frangible portion 144 may alternately or additionally be formed with macroscopic features such as honeycomb patterns, columns, or hollow channels to provide the desired frangible properties. According to the illustrated embodiment, the frangible portion 144 is of a substance and structure with relatively high resistance to axial and shear forces, but relatively low resistance to torque. In practice, shoulder joints are exposed to relatively high compressive (axial) and shear loads but relatively low torque loads. Thus, it may be important that the frangible portion 144 has enough axial and shear strength to endure typical usage of a shoulder joint, but may be broken relatively easily by intentionally torqueing the collar 104 relative to the residual peripheral portion 124 during a revision surgery in which the base 100 must be disengaged from the bone prior to implanting a secondary or revision implant. The frangible portion 144 can be designed to break under a predictable amount of stress. For example, there may be a known threshold torque force that will cause the frangible portion to break when applied to the collar 104 relative to the peripheral residual portion 124. The known threshold torque strength can be designed or chosen according to the application from factors such as which joint the implant 100 will be used to replace and the size or lifestyle of the patient. The torque strength of the frangible portion 144 may also be chosen or designed as a function of a predetermined necessary shear or axial strength. For example, the torque strength and the shear strength or axial strength of the frangible portion 144 may define at least a 1:10 ratio, such that the frangible portion will be at least ten times as strong in shear or axial load as in torque.

Breaking the collar 104 from the residual peripheral portion 124 effectively frees the collar 104 from the bone, allowing the collar 104, including central anchor 122, to be removed from the bone. Turning the collar 104 relative to the residual peripheral portion 124 will compromise or break off any ingrown bone structure, with little or no need for secondary chiseling after rotation. The collar 104 may therefore be removed from the bone to leave only the residual peripheral portion 124 behind. Removing the collar 104 provides clear access to the residual peripheral portion 124, enabling a surgeon to cut precisely around the residual peripheral portion 124, for example with a chisel, osteotome, or other suitable cutting device. As such, only a minimum amount of bone needs be removed to cut the residual peripheral portion 124 out of the bone. It is therefore possible to remove the base portion 100 while preserving much of the bone, which generally improves the success of subsequent implants.

The shape of the collar 104 and central anchor 122 in the illustrated embodiment further contribute to preservation of bone on removal. Because the collar 104 is generally cylindrical and the central anchor 122 is generally cone shaped, the collar 104 and central anchor 122 are symmetrical about the longitudinal axis X of the implant 100. The solid of revolution resulting from rotating the collar 104 and central anchor 122 around the longitudinal axis X therefore has the same, or at least nearly the same, size and shape as the collar 104 and central anchor 122. The collar 104 and central anchor 122 can therefore be rotated around the longitudinal axis X with minimal injury to surrounding bone. However, other shapes for the collar 104 and central anchor 122 beyond those illustrated here are contemplated. For example, other shapes that are symmetrical or generally symmetrical about the longitudinal axis X result in similar preservation of bone. An exterior of the central anchor 122 may optionally include features to facilitate bone ingrowth such as flutes or a porous coating.

Figure 4:
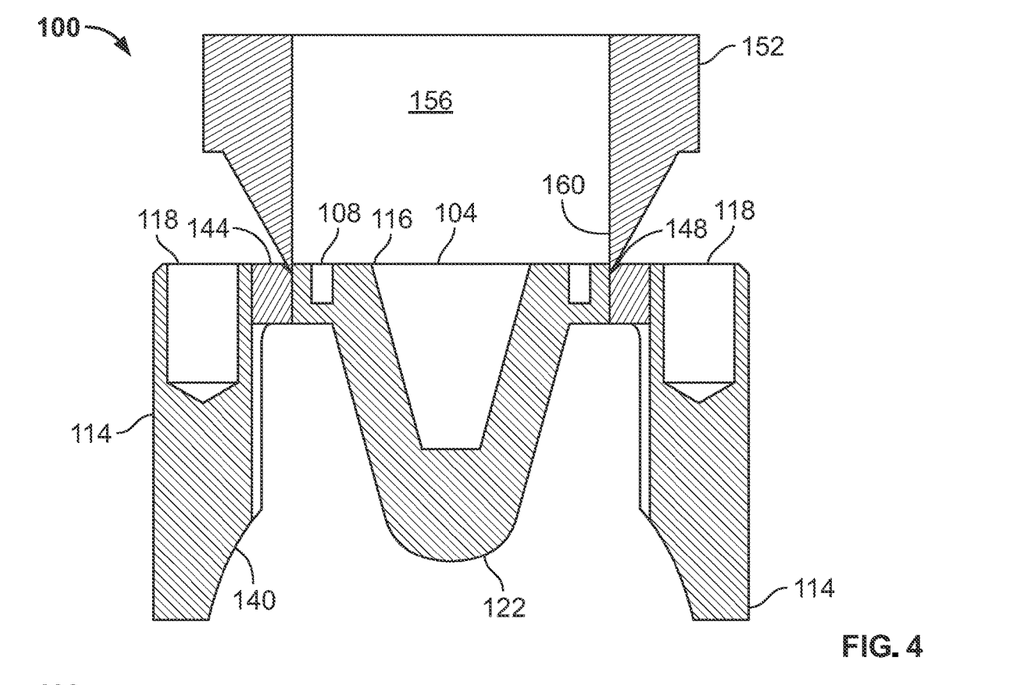
FIG. 4 illustrates a step for weakening the base member.

FIG. 4 illustrates a step for weakening or breaking the frangible portion 144. In the weakening step, a cylindrical chisel piece 152 is applied to the base member 100. The chisel piece 152 includes a cavity 156 that is approximately centered over the collar 104 and a ring wedge 160 that engages the wedge shaped recess 148 during the weakening step. An axial force is applied to the chisel piece 152, such as by striking the chisel piece 152 with a hammer, to weaken the frangible portion 144. Whether the chisel piece 152 is used to break or weaken the frangible portion 144 depends on the surgeon's preference as well as the material of the frangible portion 144. For example, in embodiments with a titanium frangible portion 144, titanium's notch sensitivity might render the frangible portion 144 breakable with the chisel piece 152. According to some embodiments, this weakening step or breaking step using the chisel piece 152 is optional or unnecessary.

Figure 5:
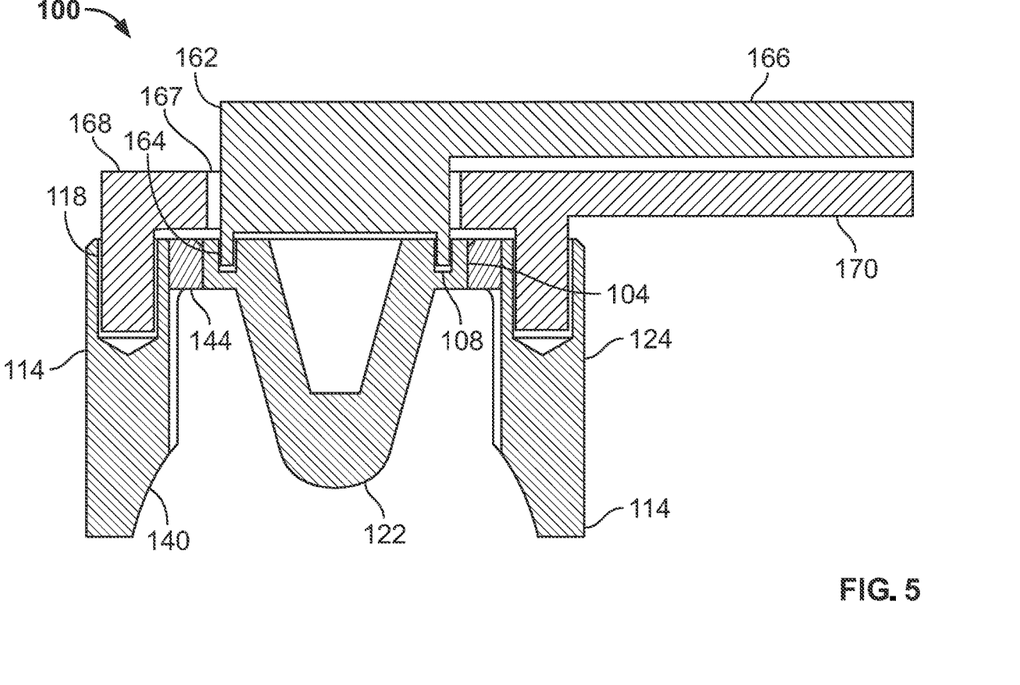
FIG. 5 illustrates a set of tools for separating the base member.

FIG. 5 shows exemplary tools for separating the collar 104 from the residual peripheral portion 124. In the illustrated example, a lever 162 engages the drive channel 108 and a fulcrum 168 engages the counter-torque holes 118. The lever 162 engages the drive channel 108 with a drive ring 164 having a shape suitable for engaging the drive channel 108. For example, in some embodiments with a hex shaped drive channel 108 as shown in FIG. 1, the drive ring 164 has a matching hex shape. The lever 162 and fulcrum 168 have a radially extending lever arm 166 and fulcrum arm 170, respectively. The fulcrum 168 of the illustrated embodiment further includes a gap 167 to accommodate the lever 162. Part of the lever 162, such as the drive ring 164, extends through the gap 167 to engage the drive channel 108. Other ways for the lever 162 and fulcrum 168 to accommodate each other are contemplated, however. For example, the lever 162 could instead include gaps through which the fulcrum 168 could engage the counter-torque holes 118. In another example, the lever 162 is disposed generally under the fulcrum 168 when the lever 162 is engaged with the drive channel 108 and the fulcrum 168 is engaged with the counter-torque holes 118.

According to the illustrated embodiment, the frangible portion 144 is broken and the collar 104 is separated from the residual peripheral portion 124 by applying torque to the collar 104 relative to the residual peripheral portion 124. Torque is applied by exerting force against the lever arm 166 to turn the lever 162 while exerting force on the fulcrum arm 170 to prevent the fulcrum 168 from turning. The resulting torque breaks the frangible portion 144, thus separating the collar 104 from the residual peripheral portion 124. It may be preferable to utilize the fulcrum 168 to stabilize the residual peripheral anchors 114 in the bone while torque is applied via the lever arm 166 to reduce the likelihood of unintentionally damaging bone from forces inadvertently applied to the bone via the peripheral anchors 114.

Figure 6:
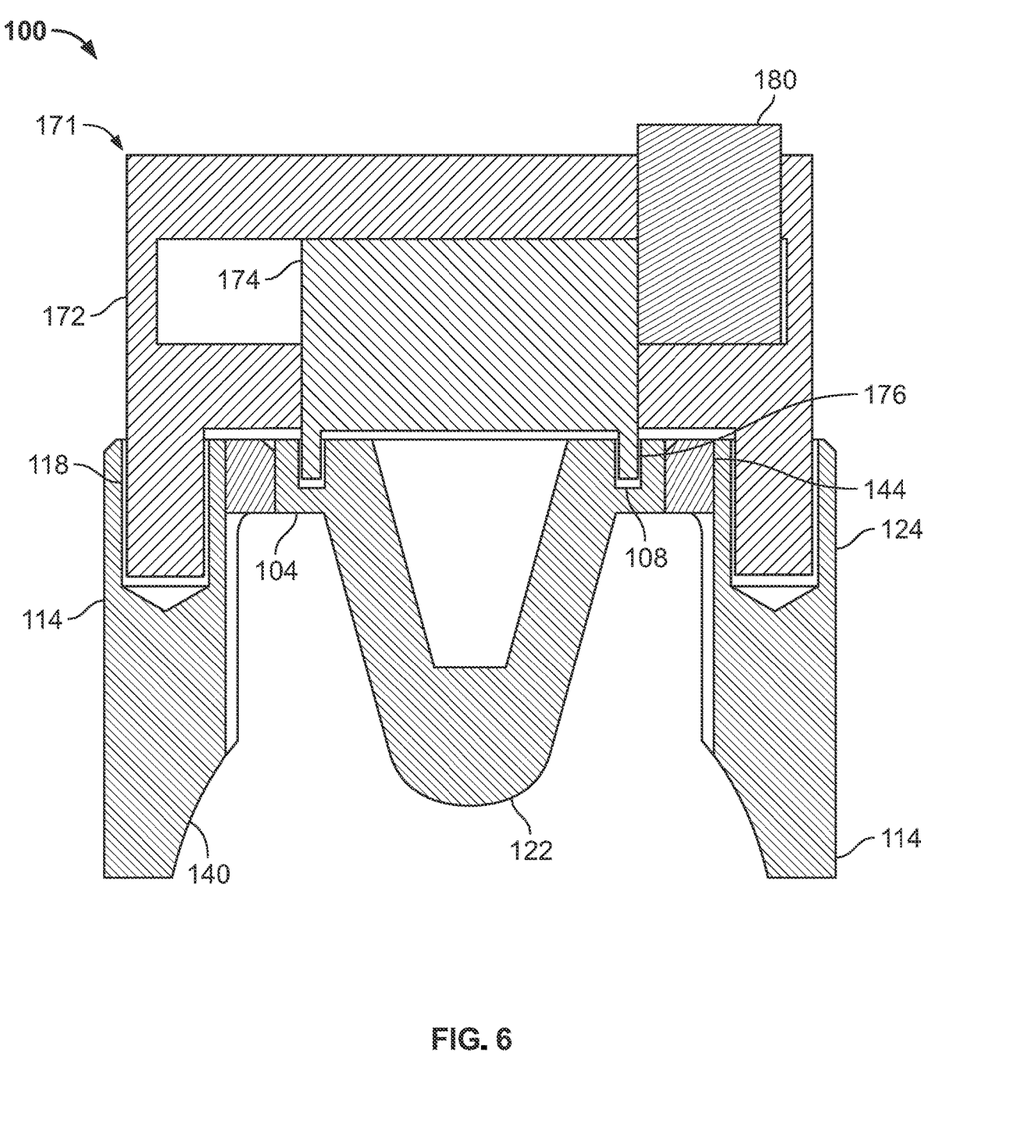
FIG. 6 illustrates an embodiment of a tool for separating the base member.

FIG. 6 illustrates another tool 171 for separating the collar 104 from the residual peripheral portion 124. A gearbox 172 engages the counter-torque holes 118 and houses a central gear 174 oriented on the longitudinal axis X of the base member 100. The central gear 174 includes a drive ring 176 that engages the drive channel 108 similarly to the drive ring 164 of the lever 162 described above. The gearbox 172 also houses a vertical input gear 180 extending parallel to and engaged with the central gear 174. In the illustrated embodiment, the input gear 180 extends axially out of the gearbox 172 in the proximal direction. In other embodiments, the input gear 180 is otherwise operably accessible from outside the gearbox 172.

The tool 171 is used to separate the collar 104 is separated from the residual peripheral portion 124 by turning the input gear 180 while the gearbox 172 engages the counter-torque holes 118 and the drive ring 176 engages the drive channel 108. Turning the input gear 180 causes the central gear 174 to turn relative to the gearbox 172, which results in torque applied to the collar 104 relative to the residual peripheral portion 124. As described above, the torque breaks the frangible portion 144 and thereby separates the collar 104 from the residual peripheral portion 124. A single input gear 180 is illustrated, but multiple input gears 180 could be used. For example, the tool 171 may include a planetary gear system wherein multiple input gears 180 function as planetary gears and the central gear 174 functions as a sun gear.

Figure 7:
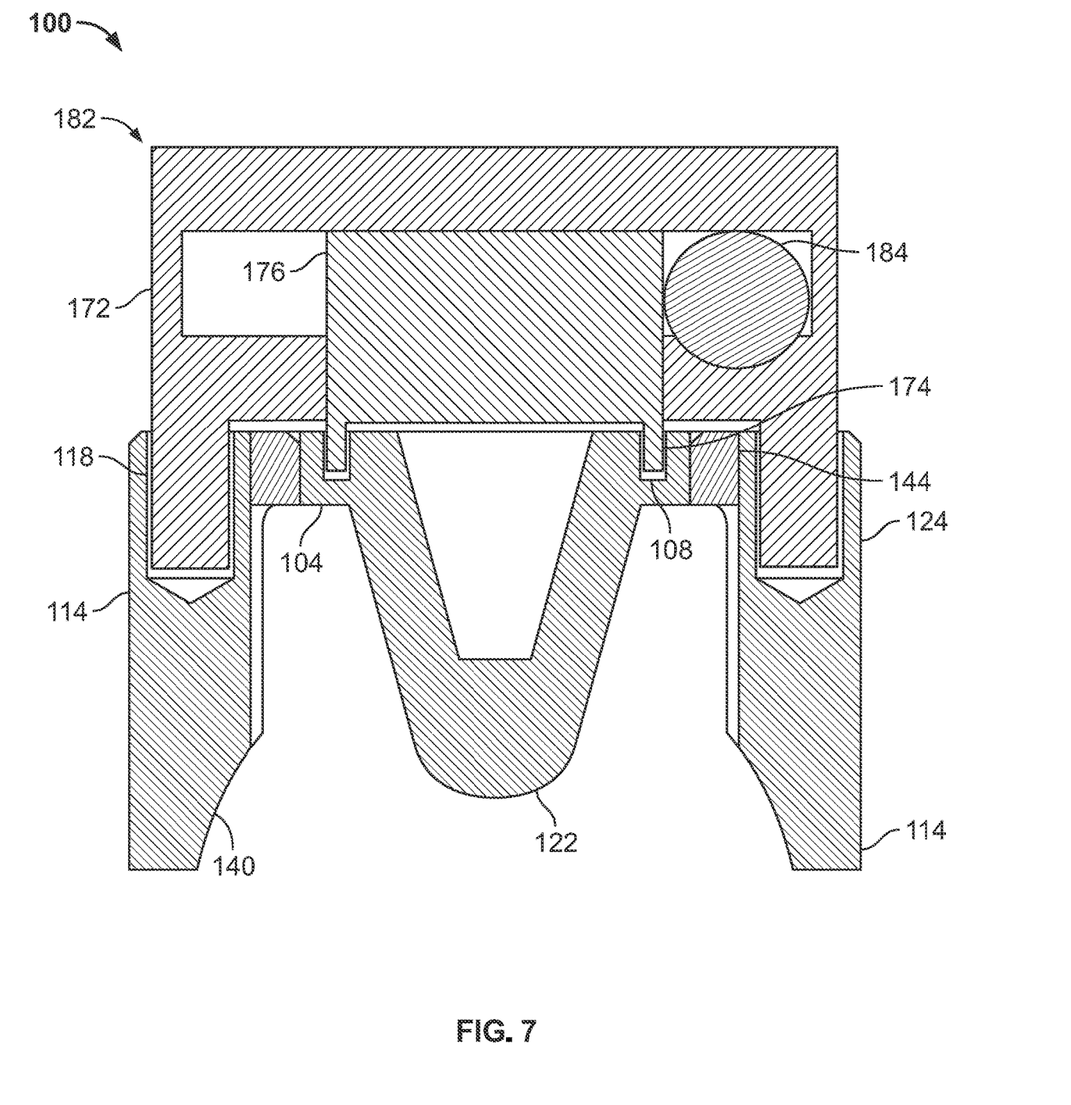
FIG. 7 illustrates another embodiment of the tool for separating the base member.

FIG. 7 illustrates a second tool 182 according to another embodiment. The second tool 182 generally operates as described above with regard to the tool 171 shown in FIG. 6. However, the second tool 182 includes a worm gear 184 instead of the input gear 180. The worm gear 184 extends perpendicular to and is engaged with the central gear 176. Similarly to the input gear 180, the worm gear 184 extends out of the gearbox 172 or is otherwise operably accessible from outside the gearbox 172. The frangible portion 144 can thus be broken and the collar 104 separated from the residual peripheral portion 124 by turning the worm gear 184 to turn the central gear 176 and generate a resulting torque on the collar 104 relative to the residual peripheral portion 124.

Figure 8:
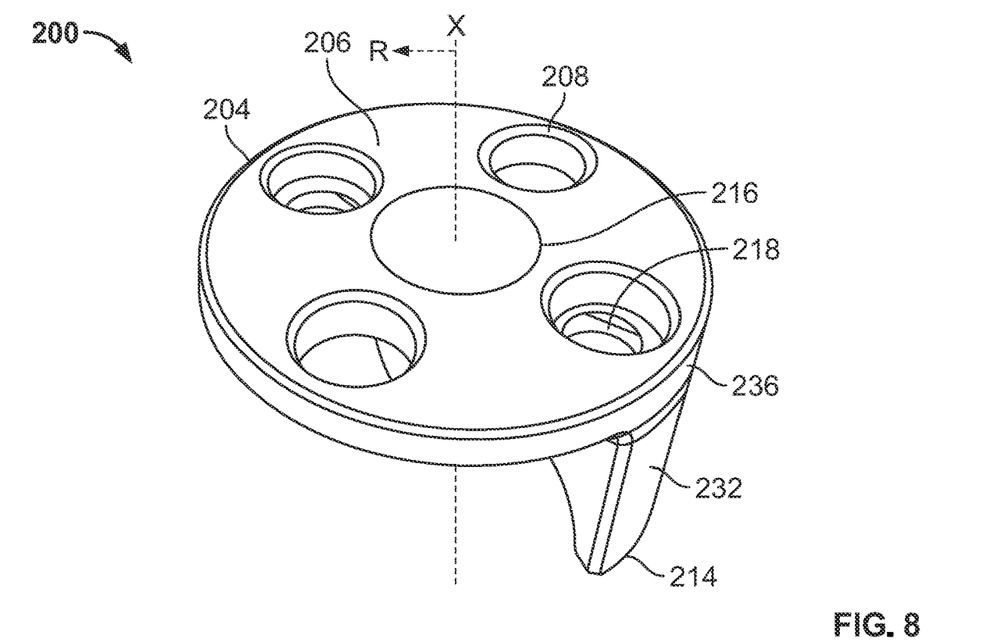
FIG. 8 is a proximal oblique view of a base member according to a second embodiment.

FIG. 8 illustrates a base member 200 according to another embodiment. The base member 200 includes a proximal collar 204 having a proximal surface 206, torque holes 208 extending axially through the collar 204 from the proximal surface 206, and an opening 216 for receiving an implant component such as, for example, a humeral head component. The base member 200 further includes peripheral anchors 214 each having a counter-torque hole 218 on a proximal surface. According to the illustrated embodiment, some of the torque holes 208 are aligned with the counter-torque holes 218, while other torque holes 208 are not.

Figure 9:
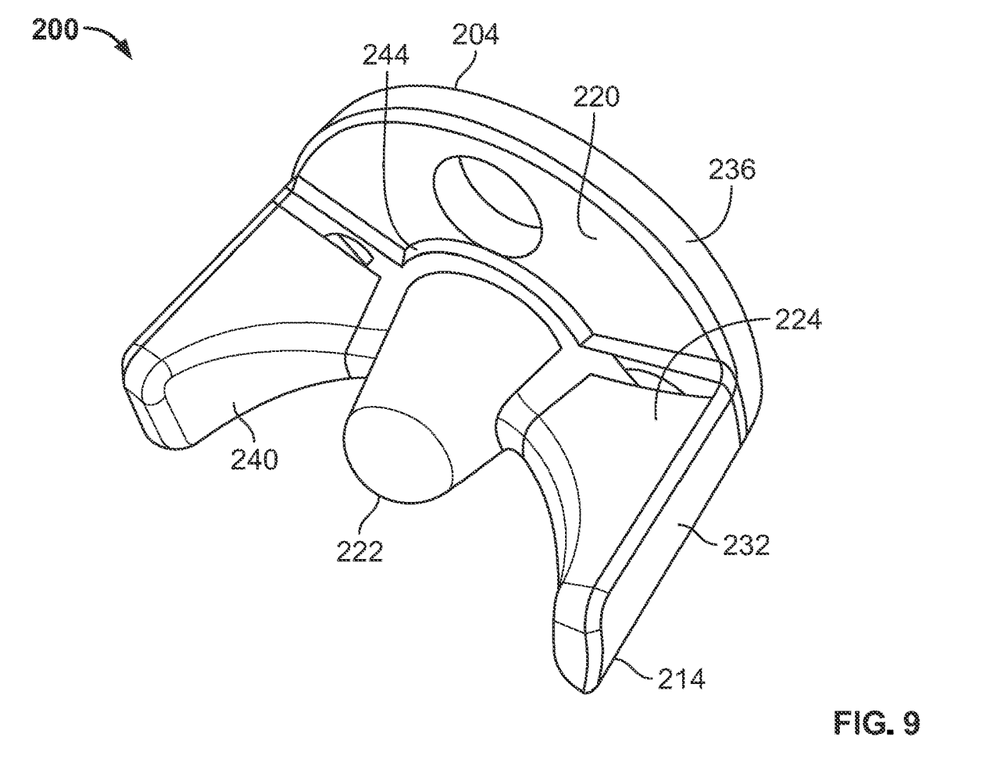
FIG. 9 is a distal oblique view of the base member according to the second embodiment.

Turning to FIG. 9, with continuing reference to FIG. 8, the collar 204 further includes a distal surface 220 and a central anchor 222 extending distally from the distal surface 220. According to the illustrated embodiment, the central anchor 222 is generally cone shaped to match the opening 216 for the implant component, generally similar to the central anchor 122 of the base 100 described above.

Figures 10, 11:
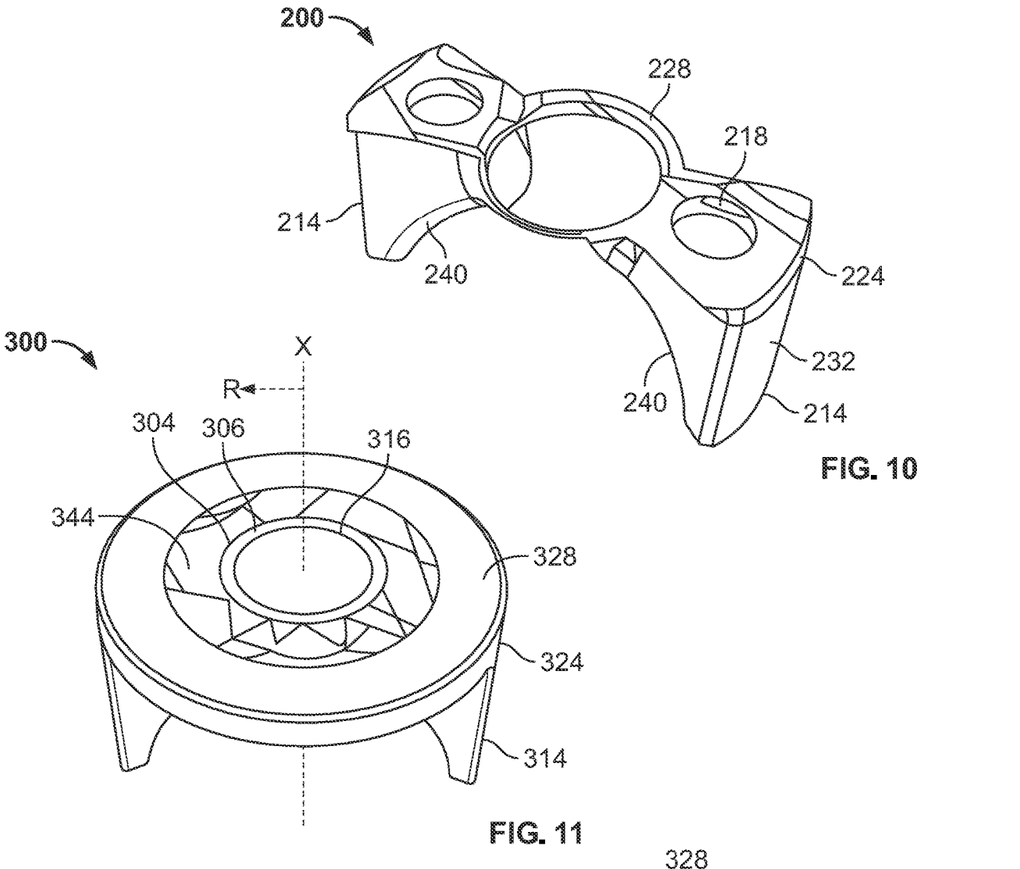
FIG. 10 illustrates a residual portion of the base member according to the second embodiment.
FIG. 11 is a proximal oblique view of a base member according to a third embodiment.

Turning to FIG. 10, with continuing reference to FIG. 9, the base member 200 further includes a residual anchor portion 224. In the illustrated embodiment, the residual anchor portion 224 includes the peripheral anchors 214 and a bridge ring 228. In an assembled base member 200, the peripheral anchor portion 224 is arranged such that the bridge ring 228 encircles the central anchor 222 and the peripheral anchors 214 extend distally from the collar 204. The peripheral anchors 214 each have an axially extending peripheral surface 232 that is radially aligned with an outer circumference 236 of the collar 204. The peripheral anchors 214 each further include an arc-shaped inner surface 240. According to the illustrated embodiment, an opposing pair of the arc shaped inner surfaces 240 generally define a half circle.

The residual anchor portion 224 is secured to the collar 204 with a frangible portion 244 such that the base member 200 is of a monolithic structure. As described above, the frangible portion 244 is generally strong and resilient with regard to linear loads, such as compressive loads in the axial direction X or shear loads in the radial direction R. However, the frangible portion 244 is relatively weak in regard to torque loads. The collar 204 may therefore be removed from the residual anchor portion 224 by applying a torque on the collar 204 relative to the residual anchor portion 224 and breaking the frangible portion 244. For example, tools could be used to non-rotatably engage the counter-torque holes 218 through torque holes 208 aligned with the counter-torque holes 218 and to rotatably engage the remaining torque holes 208. Turning the tool associated with the rotatably engaged torque holes 208 would apply torque and break the collar 204 away from the residual anchor portion 244. The collar 204 and central anchor 222 may be symmetrical about the longitudinal axis X, and therefore may have a solid of revolution around the longitudinal axis X that matches a static shape of the collar 204 and central anchor 222. As explained above, this symmetry about the longitudinal axis X contributes to preservation of bone upon torqueing and removal of the collar 204 and central anchor 222. Alternatively, the relative placement of the residual anchor portion 224 and the collar 204 allows the collar 204 to be removed from the residual portion by application of axial force in opposite directions to the residual anchor portion 224 and the collar 204. The removal with only axial force could be accomplished with a tool or tools that would engage the residual anchor portion 224 and an underside of the collar 204 through the torque holes 208.

The width of the proximal collar 204 of the present embodiment compared to the thinness of the bridge ring 228 provides increased visibility of the underlying bone upon removal of the proximal collar 204. Such increased visibility may enable a surgeon to cut around the residual anchor portion 224 with relative precision.

FIG. 11 illustrates a base member 300 according to a third embodiment. The base member 300 includes a proximal collar 304 with a proximal surface 306 and an opening 316 in the proximal surface 306 for receiving an implant component. The base member 300 further includes a residual peripheral portion 324. The residual peripheral portion 324 includes peripheral anchors 314 and a peripheral ring 328 that encircles the collar 304 and connects the peripheral anchors 314. The residual peripheral portion 324 is connected to the collar 304 by a frangible portion 344 such that the base member 300 is of a monolithic structure.

As discussed above, the frangible portion 344 is generally strong and resilient to linear loads, such as compressive loads in the axial direction X or shear loads in the radial direction R. However, the frangible portion 344 is relatively weak in regard to torque loads. The frangible portion 344 can therefore be broken to separate the collar 304 from the residual peripheral portion 324 by torqueing the collar 304 relative to the residual portion 324.

Figure 12:
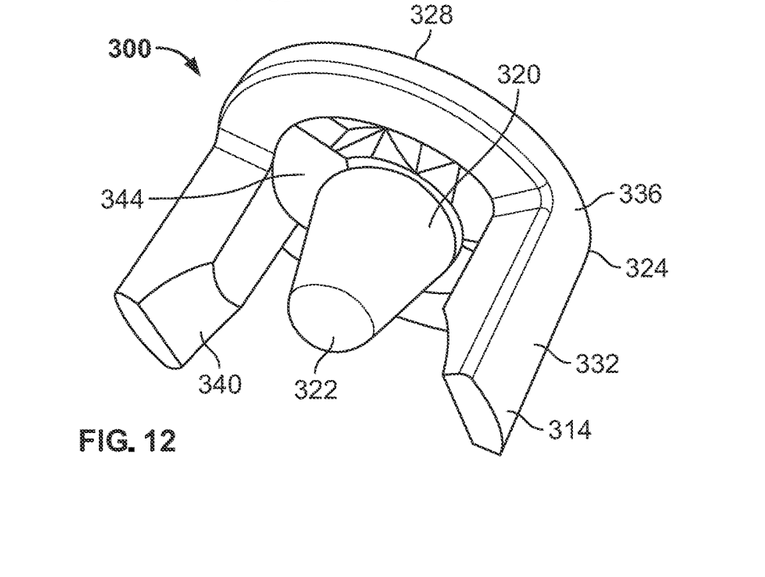
FIG. 12 is a distal oblique view of the base member according to the third embodiment.

Turning to FIG. 12, the collar 304 also includes a distal surface 320 defining a central anchor 322. In the illustrated embodiment, the central anchor 322 is generally cone shaped to match the opening 316 for receiving the implant component, similar to the embodiments described above. The collar 304 and central anchor 322 may therefore be symmetrical about the longitudinal axis X of the implant. As such, the collar 304 and central anchor 322 may have a solid of revolution about the longitudinal axis X that is the same as the static shape of the collar 304 and central anchor 322. As discussed above, the symmetry about the axis X may contribute to preservation of bone when torque is applied to the collar 304 to separate the collar 304 from the residual portion 322.

In the illustrated embodiment, each peripheral anchor 314 has an axially extending peripheral surface 332 that is radially aligned with an outer circumference 336 of the peripheral ring 328. Also according to the illustrated embodiment, each peripheral anchor 314 has an interior surface substantially parallel to the peripheral surface 332, with an arc shaped transition surface 340 connecting the peripheral surface 332 to the interior surface.

The proximal collar 304 of the present embodiment may be removed by application of torque through, for example, a tool having a generally cone-shaped output end shaped to have a friction fit within the opening 316.

For each embodiment of base 100, 200, and 300 described above, the base and a corresponding prosthetic humeral head are implanted into a patient, it may be desirable at a later time point to remove the prosthetic stemless humeral implant and to replace it with a second prosthetic humeral implant, whether stemless or stemmed, via a revision procedure. During such a revision procedure, the shoulder joint of the patient may be accessed by any suitable means and the prosthetic humeral head may first be removed from the base. Any one of the methods and/or tools described above may be used to weaken and break the frangible portion of the base so that the collar of the base is easily removed from the bone, leaving the residual portion of the base remaining in the bone. Regardless of the shape of the residual base remaining the bone, the access to that residual base is increased by virtue of removing the collar portion of the base. This increased access, as mentioned above, allows for a surgeon to more accurately and precisely cut the residual portion of the base out of the bone, for example using a chisel or osteotome, while damaging a relatively small amount of the remaining bone stock in the process. As a result, once the residual portion of the base is removed from the bone, more viable bone stock may remain than if the entire base component was explanted in a single step, without an intermediate step of breaking the collar away from the residual portion of the base. As a results, a relatively large amount of bone stock remains to provide a relatively better amount of anchoring of the secondary humeral prosthesis into the proximal humerus for the revision procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrange-

The invention claimed is:

1. A base member of a prosthetic stemless shoulder implant, the base member comprising:
   a proximal collar having a proximal surface and a distal bone-engaging surface opposite the proximal surface;
   a central anchor extending distally from the bone-engaging surface and defining an opening extending from the bone-engaging surface into the central anchor for receiving a humeral head component of the prosthetic stemless shoulder implant;
   at least one peripheral anchor positioned radially outwardly of the central anchor and extending distally from the bone-engaging surface, the peripheral anchor being frangibly connected to the proximal collar by a ring that encircles the proximal collar and a frangible portion that is located between and monolithically formed with the ring and the proximal collar.

2. The base member of claim 1, wherein the at least one peripheral anchor is frangibly connected to the central anchor.

3. The base member of claim 2, wherein the proximal collar and the central anchor are separable from the at least one peripheral anchor upon application of a threshold torque force.

4. The base member of claim 1, wherein the frangible portion has a shear strength, an axial strength, and a torque strength, and the shear strength or the axial strength are at least ten times as great as the torque strength.

5. The base member of claim 1, wherein the frangible portion connects the bone-engaging surface and the at least one peripheral anchor.

6. The base member of claim 5, wherein the frangible portion is configured to break upon application of a threshold torque force.

7. The base member of claim 5, wherein the frangible portion is a material with greater porosity than the proximal collar and the peripheral anchor.

8. The base member of claim 1, wherein a hole extends from the proximal collar into the at least one peripheral anchor for receiving a holding device to prevent rotation of the at least one peripheral anchor.

9. The base member of claim 1, wherein the base member is monolithically formed.

10. A base member of a prosthetic stemless shoulder implant, the base member comprising:
    a proximal collar having a proximal surface and a distal bone-engaging surface opposite the proximal surface;
    a central anchor extending distally from the bone-engaging surface and defining an opening extending from the bone-engaging surface into the central anchor for receiving a humeral head component of the prosthetic stemless shoulder implant;
    at least one peripheral anchor positioned radially outwardly of the central anchor and extending distally from the bone-engaging surface, the peripheral anchor being frangibly connected to the proximal collar;
    a residual portion that includes the at least one peripheral anchor and a ring that encircles the proximal collar or the central anchor; and
    a frangible portion monolithically formed with the ring and the proximal collar or the central anchor.

11. The base member of claim 10, wherein the ring is connected to at least one of the proximal collar and the central anchor by the frangible portion.

12. The base member of claim 11, wherein the frangible portion is in the shape of a ring around at least one of the proximal collar and the central anchor.

13. The base member of claim 11, wherein the proximal collar, the central anchor, and the at least one peripheral anchor include a same material.

14. The base member of claim 1, wherein the proximal collar includes a drive channel that is concentric with the proximal collar for receiving a polygonal drive element.

15. The base member of claim 7, wherein the base member is additively manufactured.

16. A method of preparing a patient for revision surgery of a prosthetic shoulder implant previously implanted into a patient, the method comprising:
    applying torque to the proximal collar of the base member of claim 1 to break the frangible portion of the base member, thereby separating the proximal collar from the at least one peripheral anchor of the base member;
    removing the proximal collar from a humerus of the patient; and
    after the collar is removed, removing the at least one peripheral anchor from the humerus of the patient.

17. The method of claim 16, further comprising application of a chisel piece to the frangible portion to weaken the frangible portion.

18. The method of claim 16, wherein applying the torque includes applying at least one tool to the base member such that a first feature of the at least one tool engages the proximal collar and a second feature of the at least one tool engages a residual portion that includes the at least one peripheral anchor.

19. The method of claim 18, wherein the at least one tool includes a lever that engages the proximal collar and a fulcrum that engages the residual portion.

20. The method of claim 18, wherein the at least one tool includes:
    a gearbox that engages the residual portion;
    a central gear disposed within the gearbox at a location concentric with the proximal collar and connected to an output feature that engages the proximal collar; and
    an input gear operatively connected with the central gear such that rotating the input gear causes the central gear to rotate relative to the gearbox.

* * * * *